(12) United States Patent
Zhou (10) Patent No.: US 11,147,676 B2
(45) Date of Patent: Oct. 19, 2021

(54) MINIMALLY INVASIVE HIP JOINT AND JOINT REPLACING METHOD

(71) Applicant: Ximing Zhou, Beijing (CN)

(72) Inventor: Ximing Zhou, Beijing (CN)

(73) Assignee: Ximing Zhou, Beijing (CN)

( * ) Notice: Subject to any disclaimer, the term of this patent is extended or adjusted under 35 U.S.C. 154(b) by 173 days.

(21) Appl. No.: 16/351,889

(22) Filed: Mar. 13, 2019

(65) Prior Publication Data
US 2020/0289273 A1   Sep. 17, 2020

(51) Int. Cl.
*A61F 2/36* (2006.01)
*A61B 17/16* (2006.01)
*A61B 17/17* (2006.01)
*A61B 17/56* (2006.01)

(52) U.S. Cl.
CPC ........ *A61F 2/3609* (2013.01); *A61B 17/1664* (2013.01); *A61B 17/1742* (2013.01); *A61B 2017/564* (2013.01); *A61F 2002/365* (2013.01); *A61F 2002/3625* (2013.01); *A61F 2002/3674* (2013.01)

(58) Field of Classification Search
CPC .............. A61F 2/3609; A61B 17/1664; A61B 17/1666; A61B 17/1668; A61B 17/1742; A61B 17/1746; A61B 17/175
See application file for complete search history.

(56) References Cited

U.S. PATENT DOCUMENTS

| | | | | |
|---|---|---|---|---|
| 5,997,582 | A * | 12/1999 | Weiss ................. | A61F 2/30756 606/89 |
| 6,375,648 | B1 * | 4/2002 | Edelman ............ | A61M 3/0279 604/265 |
| 2001/0012967 | A1 * | 8/2001 | Mosseri ............... | A61F 2/4607 623/23.12 |
| 2003/0060890 | A1 * | 3/2003 | Tarabishy .......... | A61B 17/1684 623/22.12 |
| 2006/0064164 | A1 * | 3/2006 | Thelen ............... | A61B 17/164 623/16.11 |
| 2009/0281545 | A1 * | 11/2009 | Stubbs ................ | A61B 17/175 606/87 |
| 2010/0298834 | A1 * | 11/2010 | Hildebrandt ....... | A61B 17/1703 606/80 |
| 2011/0306975 | A1 * | 12/2011 | Kaikkonen ........ | A61B 17/8858 606/63 |

(Continued)

*Primary Examiner* — Matthew J Lawson
(74) *Attorney, Agent, or Firm* — David G. Rosenbaum; Rosenbaum IP (57) ABSTRACT

A minimally invasive hip joint and a joint replacing method are provided. The minimally invasive hip joint includes a threaded rod and a joint body including a plurality of elastic sheets, with their top ends being all disposed at a top end position of the threaded rod, and bottom ends being all movably sleeved on the threaded rod and dispersedly distributed along the circumferential direction of the threaded rod; and the threaded rod is threadedly engaged with a locking component located at the below position of the elastic sheets. The joint replacing method comprises replacing a damaged or undamaged femoral head on a femur with the aforementioned minimally invasive hip joint. When replacing a damaged or undamaged femoral head with the minimally invasive hip joint, it is only necessary to drill at the outer side of the trochanter major and rotate the locking component.

6 Claims, 7 Drawing Sheets

(56) References Cited

U.S. PATENT DOCUMENTS

| | | | |
|---|---|---|---|
| 2014/0114368 A1* | 4/2014 | Lin | A61B 17/744 606/86 R |
| 2015/0112351 A1* | 4/2015 | Hsu | A61B 17/7258 606/92 |
| 2016/0135964 A1* | 5/2016 | Forsell | A61B 17/3423 600/424 |

* cited by examiner

MINIMALLY INVASIVE HIP JOINT AND JOINT REPLACING METHOD

BACKGROUND

Technical Field

The present disclosure relates to the technical field of medical equipment, and in particular to a minimally invasive hip joint and a joint replacing method.

Background Art

The hip joint is constituted by the femoral head and the acetabulum opposite to each other. It is an important joint connecting the lower limbs and the upper limbs of a human body, which directly determines the movement of the lower limbs. Hip arthroplasty is a technique in which an articular surface damaged by a disease or injury is replaced, by a surgical method, with an artificial joint similar to a human bone joint, which serves to excise the lesion, remove the pain, and restore the joint movement and the original function. Currently, after the hip joint is fractured, it is generally necessary to excise the femoral head and replace the femoral head. Since the femoral head faces the inner side of the human body, such surgery requires making a relatively large incision on the human body, which is a great injury to the patient, and the aged patients or patients with surgical contraindications can only stay in bed for a long time after the surgery and have a long convalescence or even cannot recover, causing serious harm to the basic health of the elderly.

SUMMARY OF THE INVENTION

The minimally invasive hip joint provided by the present disclosure includes a threaded rod and a joint body, the joint body including a plurality of elastic sheets, with their top ends being all disposed at a top end position of the threaded rod, and their bottom ends being all movably sleeved on the threaded rod and dispersedly distributed along the circumferential direction of the threaded rod; and the threaded rod being provided, by thread engagement, with a locking component that is located at the below position of the elastic sheets.

Embodiments of the present disclosure further provide a joint replacing method, which comprises replacing a damaged or undamaged femoral head on a femur with the above-mentioned minimally invasive hip joint, the replacing step comprising:

drilling a through hole with a drilling tool from the side of a trochanter major of the femur toward the femoral head;

inserting a cutting tool into the through hole from the side of the trochanter major, with the blade of the cutting tool protruding to the outside of the through hole, and rotating the cutting tool to enable the blade to excise the damaged or undamaged femoral head; and taking out the cutting tool;

inserting the top end of the minimally invasive hip joint in a contracted state into the through hole from the side of the trochanter major, with the elastic sheets protruding to the outside of the through hole; and rotating upward the locking component of the minimally invasive hip joint to enable the locking component to synchronously push the bottom ends of the plurality of elastic sheets upwardly, so that the plurality of elastic sheets expand outward simultaneously to form a hollow sphere so as to replace the damaged or undamaged femoral head.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In order to more clearly illustrate the technical solutions of the specific embodiments of the present disclosure or of the prior art, brief description is made below on the drawings required to be used in the description of the specific embodiments or the prior art. Obviously, the drawings described below are merely illustrative of some of the embodiments of the present disclosure, and for a person of ordinary skills in the art, other drawings may also be obtained from these drawings without inventive effort.

Reference signs: 1—threaded rod; 11—stop cap; 12—positioning nut; 2—joint body; 21—upper collar; 22—elastic sheet; 23—lower collar; 24—sleeving; 3—locking component; 31—sleeve; 311—connecting section; 3111—first threaded hole; 312—cavity section; 3121—receiving cavity; 32—locking nut; 33—retaining ring; 34—gasket; 4—cutting tool; 41—tubular body; 411—rotating groove; 42—driving component; 421—inserting rod; 422—driving rod; 43—blade; 5—fixing tool; 51—handle; 52—fixing rod; 521—second threaded hole; 6—rotating tool; 61—rotating base; 611—inlay groove; 7—drilling tool; 8—acetabulum; 9—femur; 91—trochanter major; 911—through hole; and 92—femoral head.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The technical solutions of the present disclosure will be described below clearly and completely with reference to the drawings. It is apparent that the embodiments described are some, but not all of the embodiments of the present disclosure. All the other embodiments, obtained by those ordinarily skilled in the art in light of the embodiments of the present disclosure without inventive efforts, will fall within the claimed scope of the present disclosure.

In the description of the present disclosure, it should be indicated that orientation or positional relations indicated by the terms such as "center", "up", "down", "left", "right", "vertical", "horizontal", "inside" or "outside" are based on the orientation or positional relations as shown in the drawings, only for facilitating description of the present disclosure and simplifying the description, rather than indicating or implying that the referred devices or elements must be in a particular orientation or constructed or operated in the particular orientation, and therefore they should not be construed as limiting the present disclosure.

In the description of the present disclosure, it should be indicated that unless otherwise expressly specified or defined, the terms "mount", "link" and "connect" should be understood broadly, and for example, a connection may be a fixed connection, or a detachable connection, or an integrated connection; may be a mechanical connection or an electric connection; or may be a direct linking, or an indirect linking via an intermediate medium, or may be an internal communication between two elements. The specific meanings of the above-mentioned terms in the present disclosure could be understood by those ordinarily skilled in the art according to specific situations.

The minimally invasive hip joint and the joint replacing method of the present application solve the technical problem existing in the prior art that for the patients who cannot undergo surgeries with large trauma for their own conditions, relatively great injuries will be caused at the time of replacing a free femoral head with an artificial joint.

Figure 9:
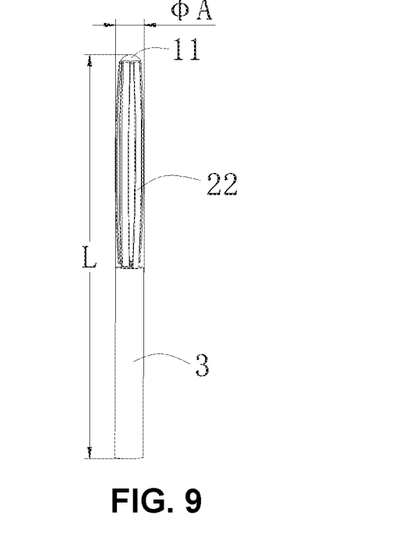
FIG. 9 is a three-dimensional structure diagram illustrating the case where the minimally invasive hip joint is in a contracted state according to an embodiment of the present disclosure.
Figure 10:
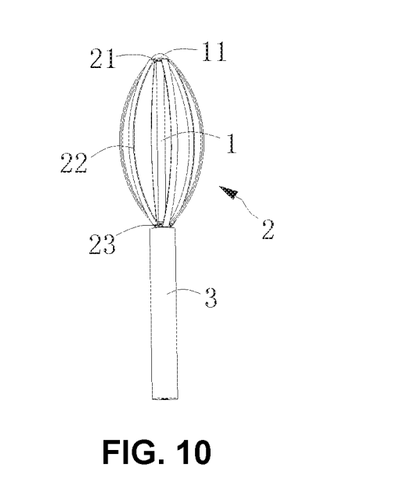
FIG. 10 is a three-dimensional structure diagram illustrating the case where the minimally invasive hip joint is in a semi-expanded state according to an embodiment of the present disclosure.
Figure 11:
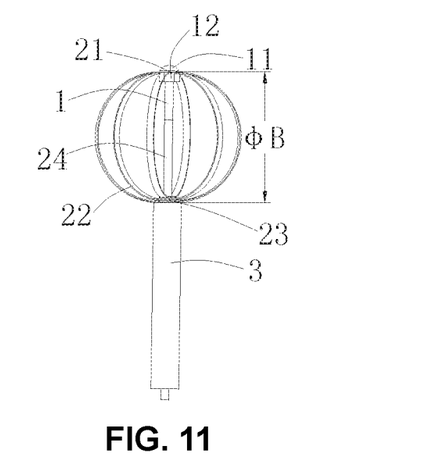
FIG. 11 is a three-dimensional structure diagram illustrating the case where the minimally invasive hip joint is in an expanded state according to an embodiment of the present disclosure.

The present embodiment provides a minimally invasive hip joint, as shown in FIG. 9 to FIG. 11, including a threaded rod 1 and a joint body 2, the joint body 2 including a plurality of elastic sheets 22, with their top ends being all disposed at the top end position of the threaded rod 1, and their bottom ends being all movably sleeved on the threaded rod 1 and dispersedly distributed along the circumferential direction of the threaded rod 1; and the threaded rod 1 being provided, by thread engagement, with a locking component 3 that is located at the below position of the elastic sheets 22.

The present embodiment also provides a joint replacing method, which comprises replacing a damaged or undamaged femoral head 92 on the femur 9 with the above-mentioned minimally invasive hip joint, the replacing step comprising: drilling a through hole 911 with a drilling tool 7 from the side of a trochanter major 91 of the femur 9 toward the femoral head 92; inserting a cutting tool 4 into the through hole 911 from the side of the trochanter major 91, with the blade 43 of the cutting tool 4 protruding to the outside of the through hole 911, and rotating the cutting tool 4 to enable the blade 43 to excise the damaged or undamaged femoral head 92; and taking out the cutting tool 4; inserting the top end of the minimally invasive hip joint in a contracted state into the through hole 911 from the side of the trochanter major 91, with the elastic sheets 22 protruding to the outside of the through hole 911; and rotating upward the locking component 3 of the minimally invasive hip joint to enable the locking component 3 to synchronously push the bottom ends of the plurality of elastic sheets 22 upwardly, so that the plurality of elastic sheets 22 expand outward simultaneously to form a hollow sphere so as to replace the damaged or undamaged femoral head 92.

For the minimally invasive hip joint and joint replacing method provided by the present embodiment, the minimally invasive hip joint comprises a threaded rod 1 acting as a connection support body, a joint body 2 capable of contracting or expanding, and a locking component 3 which controls the contraction and expansion state of the joint body 2 by moving on the threaded rod 1; wherein the joint replacing method is used to replace a damaged or undamaged femoral head 92 of a patient with the aforementioned minimally invasive hip joint.

Figure 1:
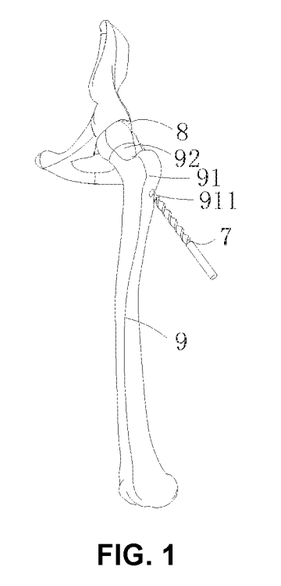
FIG. 1 is a three-dimensional structure diagram illustrating drilling on a trochanter major in a joint replacing method provided by an embodiment of the present disclosure.
Figure 2:
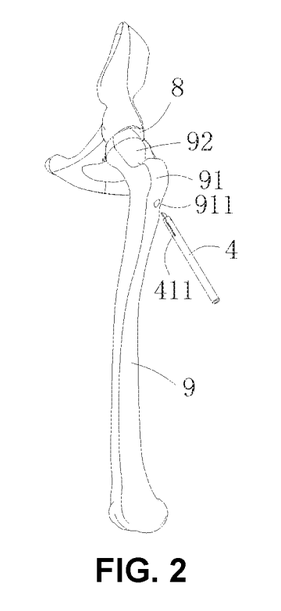
FIG. 2 is a three-dimensional structure diagram illustrating inserting a cutting tool into a through hole in the joint replacing method provided by an embodiment of the present disclosure.
Figure 5:
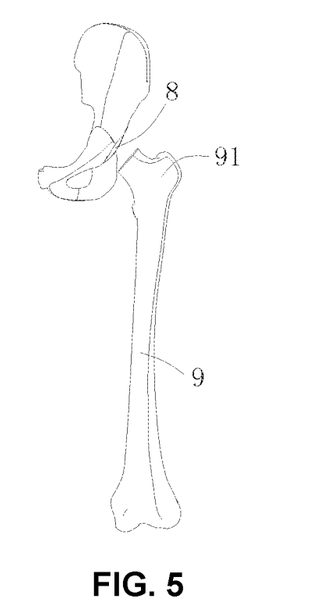
FIG. 5 is a three-dimensional structure diagram of a femur after the femoral head is excised by the cutting tool in the joint replacing method provided by an embodiment of the present disclosure.
Figure 6:
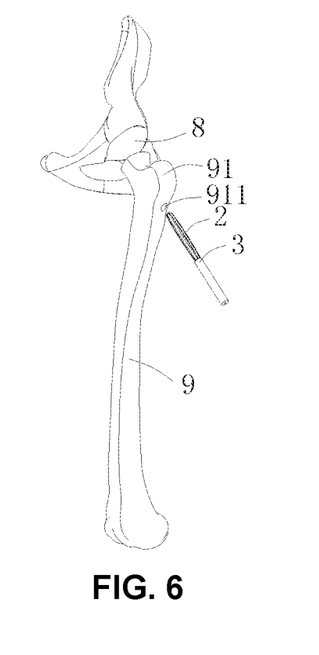
FIG. 6 is a three-dimensional structure diagram illustrating inserting a minimally invasive hip joint into the through hole in the joint replacing method provided by an embodiment of the present disclosure, wherein the minimally invasive hip joint is in a contracted state.
Figure 7:
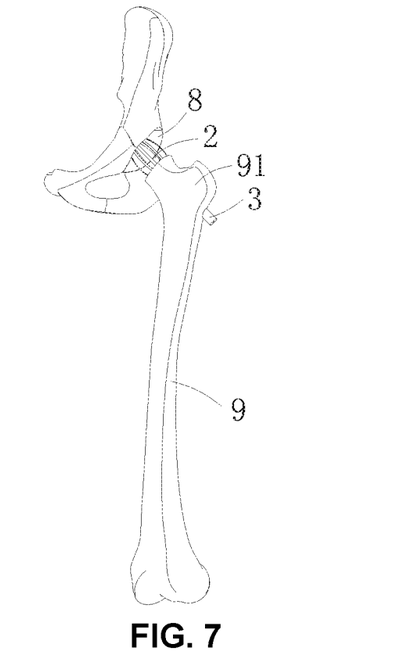
FIG. 7 is a three-dimensional structure diagram illustrating the case where the minimally invasive hip joint has been inserted into the through hole in the joint replacing method provided by an embodiment of the present disclosure, wherein the minimally invasive hip joint is in a semi-expanded state.
Figure 8:
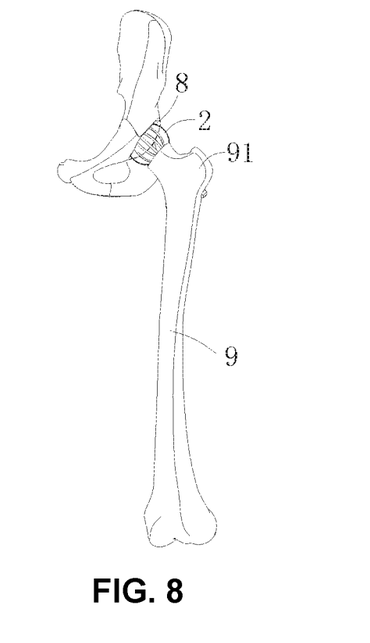
FIG. 8 is a three-dimensional structure diagram illustrating the case where the minimally invasive hip joint has been inserted into the through hole in the joint replacing method provided by an embodiment of the present disclosure, wherein the minimally invasive hip joint is in an expanded state.

When a patient's femoral head 92 is damaged or undamaged and needs to be replaced, as shown in FIG. 1, first, a through hole 911 is drilled by using the drilling tool 7 from the side of the trochanter major 91 of the patient's femur 9 toward the femoral head 92, then, as shown in FIG. 2, the cutting tool 4 is inserted into the through hole 911 from the side of the trochanter major 91, with the blade 43 of the cutting tool 4 extending to the outside of the through hole 911, the cutting tool 4 is rotated and the blade 43 excises the damaged or undamaged femoral head 92, the femur after the femoral head is excised is as shown in FIG. 5; and the cutting tool 4 is taken out and high pressure water is used to rush out the excised broken bone from the through hole 911 or other methods are adopted to remove the broken bone. Initially, as shown in FIG. 6, the locking component 3 of the minimally invasive hip joint is screwed to the bottom end position of the threaded rod 1, the elastic sheets 22 of the joint body 2 are in a freely extended state, and the entire joint body 2 is in a contracted state, then the minimally invasive hip joint has an overall look of an approximate cylinder with a relatively small outer diameter, and the outer diameter of the cylinder is smaller than the diameter of the through hole 911; the top end of the minimally invasive hip joint in the contracted state is inserted into the through hole 911 from the side of the trochanter major 91 until the elastic sheets 22 of the joint body 2 protrude to the outside of the through hole 911, and correspond to the position of the acetabulum 8; then, as shown in FIGS. 7 and 8, the locking component 3 is rotated upward, the locking component 3 synchronously pushes the bottom ends of the plurality of elastic sheets 22 upwardly, the top ends of the plurality of elastic sheets 22 are restricted and have fixed position with respect to the threaded rod 1, under the upward pushing action of the locking component 3 at the bottom end and the action of their own tension, the elastic sheets 22 expand outward simultaneously and form a hollow sphere together, and the hollow sphere acts as a new femoral head 92 to interact with the acetabulum 8, thereby completing the replacement of the damaged or undamaged femoral head 92.

When the minimally invasive hip joint needs to be removed, it is only necessary to rotate the locking component 3 downwards, the elastic sheets 22 can return to the contracted state under the action of their own tension, and the minimally invasive hip joint can just be pulled out.

In the above, in the minimally invasive hip joint, by controlling the position of the locking component 3 at the bottom end of the threaded rod 1 on the threaded rod 1, the joint body 2 can be controlled to be in a contracted state, so that the minimally invasive hip joint has an overall look of an approximate cylinder with a relatively small outer diameter, the cylinder can be inserted directly into the through hole 911 from the outside of the trochanter major 91; after the minimally invasive hip joint is mounted on the trochanter major 91, just by rotating the locking component 3, it is possible to control the joint body 2 to be in the expanded state to form a hollow sphere, which acts as the new femoral head 92 to match directly with the acetabulum 8. At the time of replacing the damaged or undamaged femoral head 92 with the above-mentioned minimally invasive hip joint, it is only necessary to drill at the outer side of the trochanter major 91 and perform a rotating operation on the locking component 3, which is convenient in operation, and can greatly reduce the trauma caused by the replacement process to the human body and correspondingly reduce the pain of the patient during the replacement process and the later recovery, as compared with the prior art practice of making a relatively large incision on the human body to enable the artificial joint for replacement to reach, from the side portion, the position where the femoral head 92 is excised, and then connecting the joint and the trochanter major 91 in the patient's body.

For aged patients or patients with surgical contraindications, the aforementioned joint replacing method can be carried out to them as soon as possible after their hip joint is fractured and damaged or undamaged, so that the patients can quickly gain basic freedom of movement under the condition of relatively minor trauma, thereby reducing or even avoiding the occurrence of the case that the patient has to stay in bed for a long time because of the large trauma due to the joint replacement; specifically, according to the actual needs of the patients, joint replacement can be performed to them in a long term.

Specifically, the elastic sheet 22 can be made of a material such as medical stainless steel or titanium alloy; as shown in FIG. 9 and FIG. 11, the contour diameter φA of the joint body 2 in the contracted state, the contour diameter φB of the joint body 2 in the expanded state, and the length L of the minimally invasive hip joint can all be selected according to the length of the patient's femur 9, the size of the femoral head 92, and the like.

It should be noted here that the orientation expressions such as "top end", "bottom end", "upper" and "lower" described herein are all defined based on the angle of view in the figures.

In the present embodiment, as shown in FIG. 9 to FIG. 11, the top end of the threaded rod 1 can be fixedly connected with a stop cap 11, an upper collar 21 is movably sleeved on the threaded rod 1, and the top ends of the plurality of elastic sheets 22 are all fixedly connected to the upper collar 21 and evenly arranged along the circumferential direction of the upper collar 21; and the lower ends of the elastic sheets 22 are fixedly connected with a lower collar 23, and the lower collar 23 is movably sleeved on the threaded rod 1. Here illustrated is one specific form in which the joint body 2 is connected to the threaded rod 1. The upper collar 21, the elastic sheets 22 and the lower collar 23 form the joint body 2, the elastic sheets 22 are provided on the threaded rod 1 by passing through the upper collar 21 and the lower collar 23, and one end of the upper collar 21 is subjected to the position-limiting effect by the stop cap 11, and one end of the lower collar 23 is subjected to the locking effect by the locking component 3. When the locking component 3 is located at the bottom end of the threaded rod 1, the lower collar 23 is unstressed, the elastic sheets 22 are in the expanded state, and the joint body 2 is in a contracted state; and after the minimally invasive hip joint is inserted into the trochanter major 91, the locking component 3 is rotated upward, the top end of the locking component 3 pushes the lower collar 23, thereby pushing the elastic sheets 22 to move upward, and the elastic sheets 22 expand outward to form a hollow sphere under the pushing action and the action of their own tension.

Specifically, the number of the upper collar 21 and the lower collar 23 may both be one. The top ends of the plurality of elastic sheets 22 are all fixedly connected to the upper collar 21, and the bottom ends thereof are all fixedly connected to the lower collar 23. At the time of installing the joint body 2, which serves as one component, it is only necessary to sleeve the upper collar 21 and the lower collar 23 on the threaded rod 1, and the installation and removal are both convenient and fast.

In addition, in the present embodiment, as shown in FIG. 9 to FIG. 11, there can be one upper collar 21 and a plurality of lower collars 23. The plurality of lower collars 23 are fixedly connected to the lower ends of the plurality of elastic sheets 22 in one-to-one correspondence, and the plurality of lower collars 23 are all movably sleeved on the threaded rod 1. Here illustrated is another form in which the elastic sheets 22 are disposed on the threaded rod 1, and the upper collar 21, the elastic sheets 22 and the lower collars 23 can be made in one piece. At the time of machining, it is feasible to fabricate the upper collar 21, the elastic sheets 22 and the lower collars 23 directly on the raw material board by cutting or other machining methods, and then bend the elastic sheets 22. The machining is convenient and fast, and the connection between the elastic sheets 22 and the upper collar 21 and between the elastic sheets 22 and the lower collars 23 is firmer; and at the time of assembling, the upper collar 21 is first sleeved on the threaded rod 1, and then the lower collars 23 at the bottom ends of the elastic sheets 22 are sleeved on the threaded rod 1 one by one.

In the present embodiment, as shown in FIG. 9 to FIG. 11, the outer end surface of the stop cap 11 may be a spherical surface. After the damaged or undamaged femoral head 92 is replaced by the minimally invasive hip joint, the outer end surface of the stop cap 11 directly contacts and matches with the patient's acetabulum 8, and the outer end surface of the stop cap 11 is a smooth spherical surface, which not only can better fit the shape of the acetabulum 8, but also can reduce the interference between the stop cap 11 and the acetabulum 8 when the minimally invasive hip joint and the acetabulum 8 rotate relative to one another, thereby improving the lubrication degree of the matching between the minimally invasive hip joint and the acetabulum 8, and reducing the pain of the patient caused by the interference therebetween.

In the present embodiment, as shown in FIG. 11, a sleeving 24 may also be sleeved on the threaded rod 1, and the outer sidewall of the sleeving 24 is correspondingly fixedly connected to the inner ring of the lower collar 23. When the locking component 3 pushes the lower collar 23 to move upward along the threaded rod 1 or when the lower collar 23 moves back downward under the tension action of the elastic sheets 22, the sleeving 24 moves synchronously with the lower collar 23 under the driving of the lower collar 23. The sleeving 24 is in direct contact with the threaded rod 1 and the contact area is relatively large, which can greatly reduce the occurrence of the case that when the lower collar 23 moves along the threaded rod 1, the lower collar 23 is easy to be caught between the threads of the threaded rod 1 due to its relatively small thickness, so as to cause relatively large resistance to the upper collar 21 relative to the threaded rod 1 and affect the expansion or contraction of the joint body 2, thereby improving the smoothness of the movement of the lower collar 23 relative to the threaded rod 1, and ensuring the normal use of the minimally invasive hip joint.

In the present embodiment, as shown in FIG. 11, the threaded rod 1 can be provided, by thread engagement, with a positioning nut 12, and the upper collar 21 is sandwiched between the positioning nut 12 and the stop cap 11. The positioning nut 12 and the stop cap 11 jointly clamp and fix the upper collar 21 at the top end of the threaded rod 1, and fixedly position the top portion of the joint body 2 to reduce the occurrence of the case that the use of the minimally invasive hip joint is influenced by the random movement of the upper collar 21 during its using process.

In the present embodiment, the locking component 3 may include a sleeve 31 and a locking nut 32 that are engaged with the threaded rod 1, and the locking nut 32 is located at a lower position of the sleeve 31. The sleeve 31 is threadedly connected to the threaded rod 1. Just by rotating the sleeve 31, it is possible to achieve the sleeve 31 tightening or loosening the bottom ends of the elastic sheets 22, thereby achieving the expansion or contraction of the elastic sheets 22. After the sleeve 31 is rotated to a set position of the threaded rod 1, the locking nut 32 is rotated to abut against the lower end of the sleeve 31, so as to lock the position of the sleeve 31 on the threaded rod 1, thereby reducing the occurrence of the case of contraction of the joint body 2 caused by reversely rotating of the sleeve 31 on the threaded rod 1.

Figure 12:
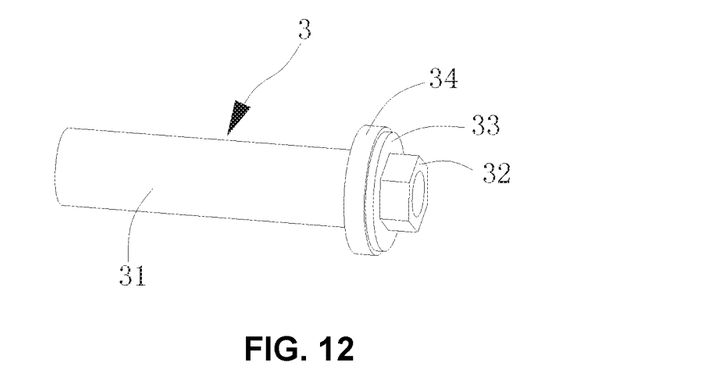
FIG. 12 is a three-dimensional structure diagram of a locking component in the minimally invasive hip joint provided by an embodiment of the present disclosure.

In addition to the above-described form in which the sleeve 31 and the locking nut 32 are two separate components, as shown in FIG. 12, in the present embodiment, the locking component 3 includes a sleeve 31 engaged with the threaded rod 1, and the bottom end of the threaded rod 1 is located inside the sleeve 31; and the bottom end of the sleeve 31 is fixedly connected with a locking nut 32. The outer surface of the sleeve 31 is a smooth curved surface, and the locking nut 32 is fixedly connected to the bottom end of the sleeve 31. When the sleeve 31 needs to be rotated, it is only necessary to rotate the locking nut 32, and the sleeve 31 can be driven to rotate synchronously, thereby reducing the occurrence of the case that it is difficult to apply a force directly to the sleeve 31, and correspondingly improving the operation convenience of the minimally invasive hip joint.

Figure 13:
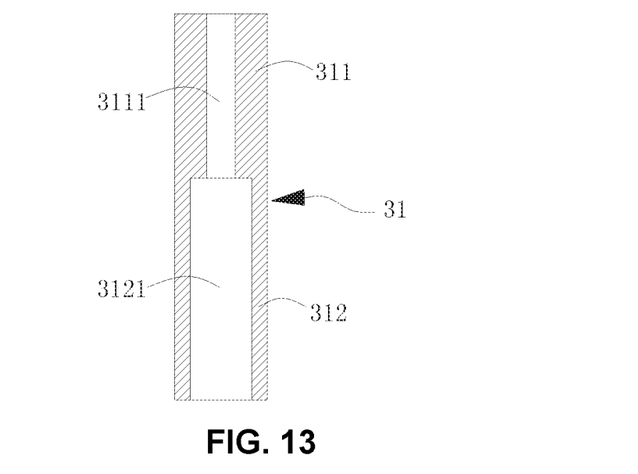
FIG. 13 is a cross-sectional structure diagram of the sleeve in FIG. 12.

In the present embodiment, as shown in FIG. 13, the sleeve 31 may include a connecting section 311 and a cavity section 312 which are sequentially connected from top to bottom. The interior of the connecting section 311 is provided, in a radial direction thereof, with a first threaded hole 3111 engaged with the threaded rod 1, the interior of the cavity section 312 is provided with a receiving cavity 3121 in a radial direction thereof, the receiving cavity 3121 is communicated with the first threaded hole 3111, and the diameter of the receiving cavity 3121 is larger than that of the first threaded hole 3111; and the bottom end of the threaded rod 1 extends into the receiving cavity 3121. Rotating the locking component 3 of the minimally invasive hip joint includes the following steps: inserting the fixing tool 5 into the receiving cavity 3121 of the sleeve 31 to fix the threaded rod 1; and rotating the locking nut 32 upward using the rotating tool 6. When it is necessary to rotate the sleeve 31, the fixing tool 5 is first inserted into the receiving cavity 3121 to be connected to the bottom end of the threaded rod 1 which extends into the receiving cavity 3121, and the operator fixes the threaded rod 1 by the fixing tool 5; and then the rotating tool 6 is used to match with the locking nut 32 and rotate the locking nut 32, and the locking nut 32 drives the sleeve 31 to rotate about the threaded rod 1, thereby achieving the sleeve 31 pushing the joint body 2. The sleeve 31 is arranged to have a connecting section 311 and a cavity section 312. While enabling threaded connection with the threaded rod 1, such arrangement, on the one hand, can ensure that the bottom end of the threaded rod 1 is located inside the sleeve 31, so as to reduce the occurrence of the case that the threaded rod 1 protrudes out of the sleeve 31 to form a sharp protrusion after the completion of the replacement, which is disadvantageous to the health and recovery of the patient and affects the use of the minimally invasive hip joint; and on the other hand, makes it possible to fix the threaded rod 1 by using the fixing tool 5 to realize the relative rotation of the sleeve 31 and the threaded rod 1, so as to reduce the occurrence of the case of the ineffective operation caused by synchronous rotation of the threaded rod 1 and the sleeve 31 when the sleeve 31 is rotated.

Figure 15:
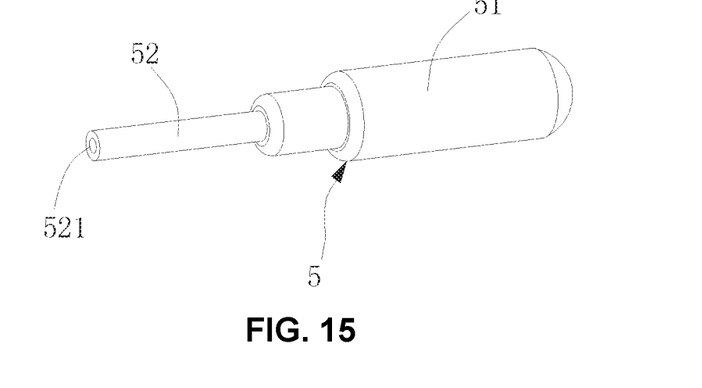
FIG. 15 is a three-dimensional structure diagram of a fixing tool in the joint replacing method provided by an embodiment of the present disclosure.

Specifically, in the present embodiment, as shown in FIG. 15, the fixing tool 5 may include a handle 51 and a fixing rod 52 fixedly connected to the handle 51, the end portion of the fixing rod 52 is provided with a second threaded hole 521 from outside to inside, and the second threaded hole 521 matches with the threaded rod 1. Fixing the threaded rod 1 by using the fixing tool 5 includes the following steps: gripping the handle 51 to insert the fixing rod 52 into the receiving cavity 3121 of the sleeve 31, and screw the fixing rod 52 into the bottom end of the threaded rod 1 through the second threaded hole 521.

Figure 14:
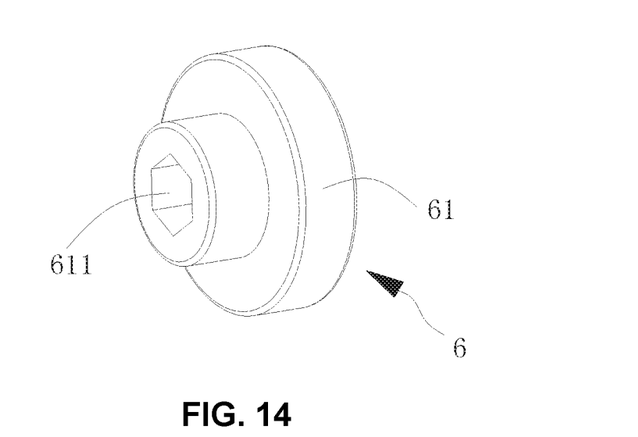
FIG. 14 is a three-dimensional structure diagram of a rotating tool in the joint replacing method provided by an embodiment of the present disclosure.

Specifically, in the present embodiment, as shown in FIG. 14, the rotating tool 6 may include a rotating base 61, the rotating base 61 is provided thereon with a rotating hole in an axial direction thereof, and is sleeved on the fixing rod 52 of the fixing tool 5 through the rotating hole; and the top end of the rotating base 61 is provided with an inlay groove 611 matching with the locking nut 32. Rotating the locking nut 32 upward by using the rotating tool 6 includes the following steps: fixedly connecting the fixing tool 5 and the threaded rod 1, sliding upward the rotating base 61 along the fixing rod 52 of the fixing tool 5, inlaying the locking nut 32 into the inlay groove 611 on the rotating base 61, and rotating the rotating base 61, so that the rotating base 61 drives the locking nut 32 and the sleeve 31 to rotate synchronously, to cause the sleeve 31 to move upward along the threaded rod 1. Here illustrated is a specific form of the rotating tool 6, and the operator applies a force to the rotating base 61 to complete the rotation of the locking nut 32 by the rotating base 61. The rotating base 61 has a larger volume than the locking nut 32, which provides higher operation convenience. Further, the outer surface of the rotating base 61 may be provided with an anti-slip stripe.

In the present embodiment, as shown in FIG. 12, a retaining ring 33 is fixedly connected between the locking nut 32 and the sleeve 31, and the diameter of the retaining ring 33 is larger than that of the sleeve 31. The minimally invasive hip joint is inserted into the through hole 911 on the trochanter major 91. The joint body 2 protrudes from the inner side of the through hole 911, and the retaining ring 33 is blocked from the outer side of the through hole 911, so that the minimally invasive hip joint is fixed on the trochanter major 91, thereby reducing the occurrence of the case that when the joint body 2 is in the expansion state, the threaded rod 1 and the sleeve 31 are tensioned to move inwardly, and as a result, the entire minimally invasive hip joint slides into the through hole 911, which affects the fixation of the relative position of the minimally invasive hip joint and the femur 9 and leads to a replacement failure. Specifically, the retaining ring 33 is made of a medical metal material.

In the present embodiment, as shown in FIG. 12, a gasket 34 may further be movably sleeved on the sleeve 31, and the diameter of the gasket 34 is not smaller than that of the retaining ring 33. When the minimally invasive hip joint is fixed on the trochanter major 91, the gasket 34 directly abuts against the outer side of the trochanter major 91, and is blocked from the outer side of the trochanter major 91. Specifically, the gasket 34 with a suitable thickness may be selected according to the extent to which the joint body 2 needs to be expanded, so that after being expanded, the minimally invasive hip joint can be firmly fixed on the trochanter major 91.

Specifically, the gasket 34 can be made of a polyethylene material which has low hardness and high smoothness, so as to reduce the abrasion on the trochanter major 91 caused by the direct contact between the metal material and the trochanter major 91, thereby reducing the pain of the patient.

Figure 3:
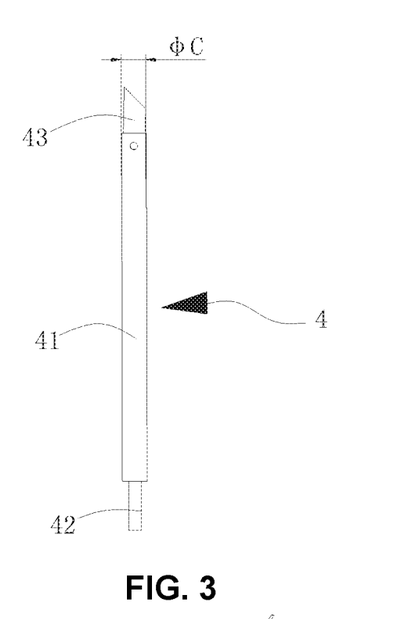
FIG. 3 is a three-dimensional structure diagram of a cutting tool in the joint replacing method provided by an embodiment of the present disclosure.

In the present embodiment, as shown in FIG. 3, the cutting tool 4 may include an internally hollow tubular body 41 and a driving component 42. The top end of the tubular body 41 is provided with a rotating groove 411 downwardly in an axial direction thereof, and the rotating groove 411 penetrates the sidewall of the tubular body 41; the blade 43 of the cutting tool 4 is inserted into the rotating groove 411 and pivoted on the sidewall of the tubular body 41; the driving component 42 is capable of being inserted into the tubular body 41 and driving the blade 43 to rotate about its pivot position; the step of excising the damaged or undamaged femoral head 92 by the cutting tool 4 includes: inserting the driving component 42 into the tubular body 41, and driving the blade 43 to rotate to a position where the blade is coaxial with the tubular body 41; inserting the cutting tool 4 into the through hole 911 on the trochanter major 91, with the blade 43 protruding to the outside of the through hole 911; controlling the driving component 42 to drive the blade 43, enabling the length direction of the blade 43 to be at an angle with the circumferential direction of the tubular body 41, and pulling out the driving component 42; rotating the tubular body 41, so that the tubular body 41 drives the blade 43 to rotate so as to enable the blade 43 to excise the femoral head 92; and after completing the excision, inserting the driving component 42 into the tubular body 41, driving the blade 43 so that the blade is coaxial with the tubular body 41, and pulling out the cutting tool 4. Specifically, the driving component 42 can drive the blade 43 to a position perpendicular to the axial direction of the tubular body 41; and for the driving component 42, the components capable of matching with the bottom end of the tubular body 41 to drive the tubular body 41 to rotate, such as an electric drill, may be selected.

The aforementioned cutting tool 4 can realize the diameter changing operation of the blade 43, and can be directly inserted into the through hole 911 from the outer side of the trochanter major 91, so as to realize the excision of the femoral head 92 without any necessity to make a relatively large incision on the human body. The cutting tool 4 is used cooperatively with a minimally invasive switch, and the entire replacement process only requires making a relatively small incision on the human body, which further reduces the trauma to the human body caused by the replacement process and reduces the pain of recovery of the patient. Specifically, the cutting tool 4 with a suitable diameter φC can be selected according to the shape and size of the patient's femoral head 92 and the volume required to be excised.

Figure 4:
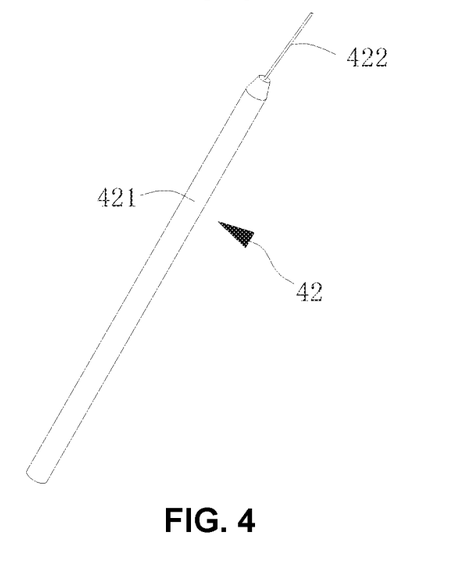
FIG. 4 is a three-dimensional structure diagram of a driving component of the cutting tool in FIG. 3.

Specifically, as shown in FIG. 4, the driving component 42 may include an inserting rod 421 and a driving rod 422 which are connected to each other, and the driving rod 422 is located at the top end of the inserting rod 421 and is disposed obliquely with respect to the inserting rod 421. Here illustrated is a specific form of the driving component 42, in which the driving rod 422 and the inserting rod 421 are arranged to be oblique relative to one another, when the driving rod 422 and the inserting rod 421 are inserted into the tubular body 41, the inserting rod 421 matches with the inner hole of the tubular body 41, when the projection of the driving rod 422 on the cross section of the tubular body 41 coincides with one side of the blade 43 by rotating the inserting rod 421, the inserting rod 421 is pushed upward, and the driving rod 422 can abut against the one side of the blade 43, the inserting rod 421 is continued to be pushed, and the driving rod 422 synchronously pushes the one side of the blade 43, and this side of the blade 43 is stressed to rotate around the pivot position to realize the angle adjustment of the blade 43, thereby completing the rotational driving of the blade 43 with respect to the tubular body 41.

Specifically, in the present embodiment, the inserting rod 421 matches, in terms of a diameter, with the cavity inside the tubular body 41. The inserting rod 421 matches with the cavity inside the tubular body 41, and is always concentrically arranged with the cavity during the rotation of the inserting rod 421, thereby improving the positional accuracy of the driving rod 422 when it is rotated with the inserting rod 421, and reducing the occurrence of the case that the positions of the driving rod 422 and the blade 43 cannot match, which is caused by the shaking of the inserting rod 421 in the cavity.

Specifically, the tubular body 41, the blade 43 and the driving component 42 of the cutting tool 4 may all be made of medical metal.

The beneficial effects of the minimally invasive hip joint and the joint replacing method of the present disclosure are as follows:

for the minimally invasive hip joint and joint replacing method provided by the present disclosure, the minimally invasive hip joint comprises a threaded rod acting as a connection support body, a joint body capable of contracting or expanding, and a locking component which controls the contraction and expansion state of the joint body by moving on the threaded rod; wherein the joint replacing method is used to replace a damaged or undamaged femoral head of a patient with the aforementioned minimally invasive hip joint.

When a patient's femoral head is damaged or undamaged and needs to be replaced, first, a through hole is drilled by using a drilling tool from the side of the trochanter major of the patient's femur toward the femoral head, then a cutting tool is inserted into the through hole from the side of the trochanter major, with the blade of the cutting tool extending to the outside of the through hole, the cutting tool is rotated and the blade excises the damaged or undamaged femoral head; and the cutting tool is taken out and high pressure water is used to rush out the excised broken bone from the through hole or other methods are adopted to remove the broken bone. Initially, the locking component of the minimally invasive hip joint is screwed to the bottom end position of the threaded rod, the elastic sheets of the joint body are in a freely extended state, and the entire joint body is in a contracted state, then the minimally invasive hip joint has an overall look of an approximate cylinder with a relatively small outer diameter, and the outer diameter of the cylinder is smaller than the diameter of the through hole; the top end of the minimally invasive hip joint in the contracted state is inserted into the through hole from the side of the trochanter major until the elastic sheets of the joint body protrude to the outside of the through hole, and correspond to the position of the acetabulum; then, the locking component is rotated upward, the locking component synchronously pushes the bottom ends of the plurality of elastic sheets upwardly, the top ends of the plurality of elastic sheets are restricted and have fixed position with respect to the threaded rod, under the upward pushing action of the locking component at the bottom end and the action of their own tension, the elastic sheets expand outward simultaneously and form a hollow sphere together, and the hollow sphere acts as a new femoral head to interact with the acetabulum, thereby completing the replacement of the damaged or undamaged femoral head.

When the minimally invasive hip joint needs to be removed, it is only necessary to rotate the locking component downwards, the elastic sheets can return to the contracted state under the action of their own tension, and the minimally invasive hip joint can just be pulled out.

In the above, in the minimally invasive hip joint, by controlling the position of the locking component at the bottom end of the threaded rod on the threaded rod, the joint body can be controlled to be in a contracted state, so that the minimally invasive hip joint has an overall look of an approximate cylinder with a relatively small outer diameter, the cylinder can be inserted directly into the through hole from the outside of the trochanter major; after the minimally invasive hip joint is mounted on the trochanter major, just by rotating the locking component, it is possible to control the joint body to be in the expanded state to form a hollow sphere, which acts as the new femoral head to match directly with the acetabulum. At the time of replacing the damaged or undamaged femoral head with the above-mentioned minimally invasive hip joint, it is only necessary to perform operation by drilling at the outer side of the trochanter major, and there is no necessity to make a relatively large incision on the human body, so as to enable the artificial joint for replacement to reach, from the side portion, the position where the femoral head is excised, and then connect the joint and the trochanter major in the patient's body. In this way, the trauma caused by the replacement process to the human body is greatly reduced, and the pain of the patient during the replacement process and the later recovery is correspondingly reduced.

For aged patients or patients with surgical contraindications, the aforementioned joint replacing method can be carried out to them as soon as possible after their hip joint is fractured and damaged or undamaged, so that the patients can quickly gain basic freedom of movement under the condition of relatively minor trauma, thereby reducing or even avoiding the occurrence of the case that the patient has to stay in bed for a long time because of the large trauma due to the joint replacement; specifically, according to the actual needs of the patients, joint replacement can be performed to them in a long term.

Finally, it should be noted that the above embodiments are only used to illustrate the technical solutions of the present disclosure, rather than limiting the same; although the present disclosure has been described in detail with reference to the foregoing embodiments, those ordinarily skilled in the art should understand that: it is still possible to modify the technical solutions described in the foregoing embodiments or equivalently replace some or all of the technical features therein; and these modifications or replacements do not deviate the essence of the corresponding technical solutions from the scope of the technical solutions of the embodiments of the present disclosure.

INDUSTRIAL APPLICABILITY

In the minimally invasive hip joint and joint replacing method provided by the present embodiment, at the time of replacing the damaged or undamaged femoral head, it is only necessary to drill at the outer side of the trochanter major and perform the rotating operation on the locking component, the operation is convenient and fast, and the replacement process causes less trauma to the human body and the patient is able to quickly gain the basic freedom of movement.

What is claimed is:

1. A joint replacing method, comprising replacing a damaged or undamaged femoral head on a femur with a minimally invasive hip joint, wherein the minimally invasive hip joint comprises a threaded rod and a joint body, wherein the joint body comprises a plurality of elastic sheets, top ends of the plurality of elastic sheets are all disposed at a top end position of the threaded rod, and bottom ends of the plurality of elastic sheets are all movably sleeved over the threaded rod and dispersedly distributed along a circumferential direction of the threaded rod and the threaded rod is provided, by thread engagement, with a locking component that is located at a below position of the elastic sheets;

the replacing step further comprises the steps of:
drilling a through hole with a drilling tool from a side of a trochanter major of the femur toward the femoral head;
inserting a cutting tool into the through hole from the side of the trochanter major, with a blade of the cutting tool protruding to an outside of the through hole, and rotating the cutting tool to enable the blade to excise the damaged or undamaged femoral head; and taking out the cutting tool;
inserting a top end of the minimally invasive hip joint in a contracted state into the through hole from the side of the trochanter major, with the elastic sheets protruding to the outside of the through hole; and
rotating upward the locking component of the minimally invasive hip joint to enable the locking component to synchronously push the bottom ends of the plurality of elastic sheets upwardly, so that the plurality of elastic sheets expand outward simultaneously to form a hollow sphere for replacement of the damaged or undamaged femoral head, wherein the cutting tool comprises an internally hollow tubular body and a driving component, a top end of the tubular body is provided downward with a rotating groove in an axial direction thereof, and the rotating groove penetrates a sidewall of the tubular body; and the blade of the cutting tool is inserted into the rotating groove and pivoted on the sidewall of the tubular body;

the driving component is capable of being inserted into the tubular body and driving the blade to rotate about its pivot position;

the step of excising the damaged or undamaged femoral head by the cutting tool comprises:
inserting the driving component into the tubular body, and driving the blade to rotate to a position at which the blade is coaxial with the tubular body;
inserting the cutting tool into the through hole on the trochanter major, with the blade protruding to the outside of the through hole;
controlling the driving component to drive the blade, such that a length direction of the blade and the circumferential direction of the tubular body form an angle therebetween, and extracting the driving component;
rotating the tubular body, so that the tubular body drives the blade to rotate so as to enable the blade to excise the femoral head; and
inserting the driving component into the tubular body after completing an excision, driving the blade to be coaxial with the tubular body, and extracting the cutting tool.

2. The joint replacing method according to claim 1, wherein the locking component comprises a sleeve, and the sleeve comprises a connecting section and a cavity section connected in sequence from top to bottom, the connecting section is provided therein, in a radial direction thereof, with a first threaded hole engaged with the threaded rod, the cavity section is provided therein, in a radial direction thereof, with a receiving cavity communicated with the first threaded hole, and a bottom end of the cavity section is fixedly connected with a locking nut;

rotating the locking component of the minimally invasive hip joint comprises following steps:
inserting a fixing tool into the receiving cavity of the sleeve to fix the threaded rod; and
rotating upward the locking nut using a rotating tool.

3. The joint replacing method according to claim 2, wherein the fixing tool comprises a handle and a fixing rod fixedly connected to the handle, an end portion of the fixing rod is provided with a second threaded hole from outside to inside, and the second threaded hole matches with the threaded rod;

the fixing the threaded rod with the fixing tool comprises following steps:
gripping the handle to insert the fixing rod into the receiving cavity of the sleeve, and screw the same into a bottom end of the threaded rod through the second threaded hole.

4. The joint replacing method according to claim 3, wherein the rotating tool comprises a rotating base, and the rotating base is provided thereon with a rotating hole in an axial direction thereof, and is sleeved on the fixing rod of the fixing tool through the rotating hole; and a top end of the rotating base is provided with an inlay groove matching with the locking nut;

the rotating upward the locking nut using the rotating tool comprises following steps:

fixedly connecting the fixing tool and the threaded rod, sliding upward the rotating base along the fixing rod of the fixing tool, inlaying the locking nut into the inlay groove on the rotating base, and rotating the rotating base, so that the rotating base drives the locking nut and the sleeve to rotate synchronously, to enable the sleeve to move upward along the threaded rod.

5. The joint replacing method according to claim 1, wherein the driving component comprises an inserting rod and a driving rod connected to each other, and the driving rod is located at a top end of the inserting rod and is disposed obliquely with respect, to the inserting rod.

6. The joint replacing method according to claim 5, wherein the inserting rod matches, in terms of a diameter, with a cavity inside the tubular body.

\* \* \* \* \*